(12) United States Patent
Gough et al.

(10) Patent No.: US 7,522,951 B2
(45) Date of Patent: Apr. 21, 2009

(54) ELECTRODE ARRANGEMENT

(75) Inventors: Paul A. Gough, Smallfield (GB); Matthew J. Bickerton, Redhill (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 443 days.

(21) Appl. No.: 10/540,594

(22) PCT Filed: Dec. 11, 2003

(86) PCT No.: PCT/IB03/05963

§ 371 (c)(1),
(2), (4) Date: Jun. 23, 2005

(87) PCT Pub. No.: WO2004/058346

PCT Pub. Date: Jul. 15, 2004

(65) Prior Publication Data

US 2006/0094948 A1    May 4, 2006

(30) Foreign Application Priority Data

Dec. 27, 2002   (GB) ................................. 0230361.8

(51) Int. Cl.
*A61B 5/04*   (2006.01)
(52) U.S. Cl. ........................ 600/388; 600/393; 600/395
(58) Field of Classification Search ................. 600/372, 600/388, 395
See application file for complete search history.

(56) References Cited

U.S. PATENT DOCUMENTS 3,954,100 A * 5/1976 Sem-Jacobsen ............. 600/393
3,993,049 A * 11/1976 Kater ........................... 600/391
4,580,572 A    4/1986 Granek et al.
4,583,547 A    4/1986 Granek et al.
4,729,377 A    3/1988 Granek et al.
5,427,096 A * 6/1995 Bogusiewicz et al. ....... 600/396
5,746,207 A    5/1998 McAdams et al.
5,944,685 A    8/1999 Masahisa
2004/0073104 A1   4/2004 Brun del re et al.
2004/0138546 A1*  7/2004 Reho et al. .................. 600/382
2006/0183990 A1*  8/2006 Tolvanen ..................... 600/386

FOREIGN PATENT DOCUMENTS

EP    0 128 103 A    12/1984
WO    WO 01 02052 A   1/2001
WO    WO 02 065904 A   8/2002

OTHER PUBLICATIONS

Translation of EP 0 128 103 A.
US 4,580,572 corresponds to EP 0 128 103.
US 4,583,547 corresponds to EP 0 128 103.
US 4,729,377 corresponds to EP 0 128 103.

* cited by examiner

*Primary Examiner*—Lee S Cohen
(74) *Attorney, Agent, or Firm*—Yan Glickberg

(57) ABSTRACT

An electrode arrangement (10) comprises a knitted electrically conductive electrode portion (12) containing electrically conductive yarn and at least one portion (14) of moisture impermeable electrically conductive material attached to the electrode portion (12). During use the electrode portion (12) and portion of material (14) are applied to a wearers skin. The moisture impermeable material portion (14) is of silicon loaded with carbon black. The moisture impermeable portion (14) encourages perspiration of a user and the perspiration trapped between the skin and moisture impermeable portion (14) reduces skin to electrode contact resistance to increase efficiency of detection of user heart rate or other electrical signals generated by a user.

16 Claims, 3 Drawing Sheets

ELECTRODE ARRANGEMENT

The present invention relates to performance improvements in substantially fabric based electrodes.

WO-A-01/02052 relates to a garment comprising at least two zones; one being formed of electrically insulative yarns and the other being formed of one or more electrically conductive yarns. The zone comprising electrically conductive yarns is intended to function as an electrode surface for contacting the corpus. Therefore the zone comprising electrically conductive yarns is present on the inner side of the garment, which is to contact the corpus skin. WO-A-01/02052 states that an electro-conductive gel can be used between the zone containing the electrically conductive yarns and the skin to assist the electrical contact between yarn and skin. It is not always desirable to introduce such gel between an electrode and the skin for a number of reasons, but in any case people are not always happy to apply a liquid or gel to a fabric based article.

Trials conducted with a textile based electrode (of which the electrode of WO-A-01/02052 is an example) fitted to a wearer have shown that the electrical resistance between the conductive portion of the textile based electrode and the skin of a wearer to which the electrode is applied is high enough to render detection of electrical signals corresponding to the wearers heartbeat very difficult. These signals are of the type that can be used to generate an electrocardiogram. The difficulty in detecting these electrical signals is not helped when there is an upper limit on the percentage of electrically conductive material that can be present in the electrode conductive portion, either for reasons of limitations imposed by the manufacturing process or because the feel or other physical property of the conductive portion would be adversely affected.

It is an object of the present invention to provide a substantially fabric based electrode arrangement with improved performance in comparison with a fabric based electrode not benefiting from the present invention.

In accordance with a first aspect of the present invention there is provided a fabric electrode arrangement exhibiting a first surface for application to the skin of a mammal, wherein said fabric electrode arrangement comprises at least one portion of material being substantially impermeable to moisture, said material being located on said first surface.

Because the at least one portion of material is substantially impermeable to moisture, the act of placing that material on the wearers skin would restrict the amount by which the skin underneath is able to breath. During use of the electrode arrangement, the at least one portion of material is positioned on the wearers skin which promotes gathering of perspiration between the skin and the portion of material by virtue of restricting the degree to which that skin is able to breath. A person secretes moisture from their skin naturally but moreover when a person takes exercise the exertion causes a person to perspire and the at least one portion of material traps perspiration between itself and the skin. The presence of the moisture or perspiration reduces the electrical resistance present between the skin and portion of material and so in turn reduces the electrical resistance present between the skin and electrode arrangement. The reduction in electrical resistance allows more efficient detection of electrical signals that may be associated with the body of a wearer, such as electrical signals corresponding to the heartbeat of the wearer, which may be used to produce an electrocardiogram. The increased efficiency of detection has the potential to allow more reliable measurement of the electrical signals under a wider variety of conditions therefore improving reliability of measurement, facilitating the measurement of signals in circumstances where it would otherwise not be possible to perform successful measurement, or allowing use of less sensitive lower cost measuring apparatus.

In cases where the electrode arrangement is to be used in or in conjunction with fitness measuring equipment, sports training aids, exercise equipment or other such equipment where a user will undergo physical exertion, the electrode of the present invention will contribute to more efficient detection of user signals, especially during the early stages of exertion. Tests have revealed that a basic knitted electrode of the type generally described by WO-A-01/02052 does not perform as well during early stages of user activity but performs much better once a user begins to perspire appreciably, thereby moistening the basic electrode and reducing the electrical resistance between the basic electrode and the wearers skin. Therefore, in cases where the electrode arrangement is to be used for monitoring a patient who is not exercising, the electrode arrangement of the present invention provides detection of user signals when the basic knitted electrode of the type generally described by WO-A-01/02052 may not.

Furthermore, the applicants have found that fabric based electrodes can exhibit electrical noise when distorted as can occur during stretching or bending of the fabric electrode. In the case of the electrode of the present invention, the increased efficiency of detection of electrical signals made possible by promoting reduction of the resistance between the skin and electrode arrangement helps to avoid or reduce the effects of such noise causing undesirable masking of the users electrical signals or otherwise interfering with the detection of such signals, which latter case can confuse signal processing apparatus.

Optionally, said at least one portion of material is located directly on said first surface. Otherwise, one or more intermediate layers of further material may be present between the one portion and said first surface.

Optionally, said at least one portion of material can be bonded to said first surface. Bonding may be performed with or without the addition of further bonding material.

Preferably, the material is mechanically flexible. Thus, the at least one portion of material is able to flex in sympathy with the first surface of the electrode arrangement.

The said material may exhibit a resistivity of less than 500 ohms per square.

However, an important property is the electrical resistance across the thickness of the material, that is the dimension between the surface for contacting the users skin and the surface for contacting the first surface of the fabric electrode. Ideally this resistance is as low as possible but a value of a few 10's of Ohms to a few hundred Ohms is tolerable. Typically the thickness is in the order of a few mm.

In one optional implementation, said material is silicone rubber loaded with conductive material. The conductive material can be carbon black or silver powder.

In a preferred arrangement, the at least one portion or a plurality of such portions collectively occupy a proportion of between one fifth and one half inclusive of that area of the first surface intended to be applied to the skin.

In general it is desirable that the presence of the at least one portion of material or plurality of such portions does not detract from the inherent advantages of a fabric electrode; these include the electrode being flexible, mechanically elastic and allowing the wearers skin to breathe thereby contributing to user comfort. In respect of this last advantage, the at least one portion of material reduces the ability of the skin to breath so the area of the first surface occupied by the portion or portions of material needs to be chosen to strike a good balance between providing an electrode arrangement which generally allows the skin to breath but which promotes gathering of perspiration in specific regions to reduce electrical contact resistance between the skin and electrode.

The said electrode can be of a knitted construction or a woven construction. Thus by choice of appropriate materials the electrode can be made comfortable for a user to wear and also permits a fair degree of breathing of the skin covered by the electrode.

The said electrode can be integral with a garment which permits the garment and electrode to be mass produced in a cost-effective manner. Furthermore an electrode that is integral with a garment also permits low profile or more elegant structures to be realised.

In accordance with second aspect of the invention there is provided a substantially textile article comprising the fabric electrode arrangement.

In accordance with a third aspect of the present invention there is provided a wearable article comprising the fabric electrode arrangement.

In accordance with a fourth aspect of the present invention there is provided a garment comprising a fabric electrode arrangement exhibiting a first surface for application to the skin of a mammal, wherein said fabric electrode arrangement comprises at least one portion of material being substantially impermeable to moisture, said material being located on said first surface.

These and other aspects of the present invention appear in the appended claims to which the reader is now referred and which are incorporated herein by reference.

The present invention will now be described with reference to the Figures of the accompanying drawings in which.

Figure 1:
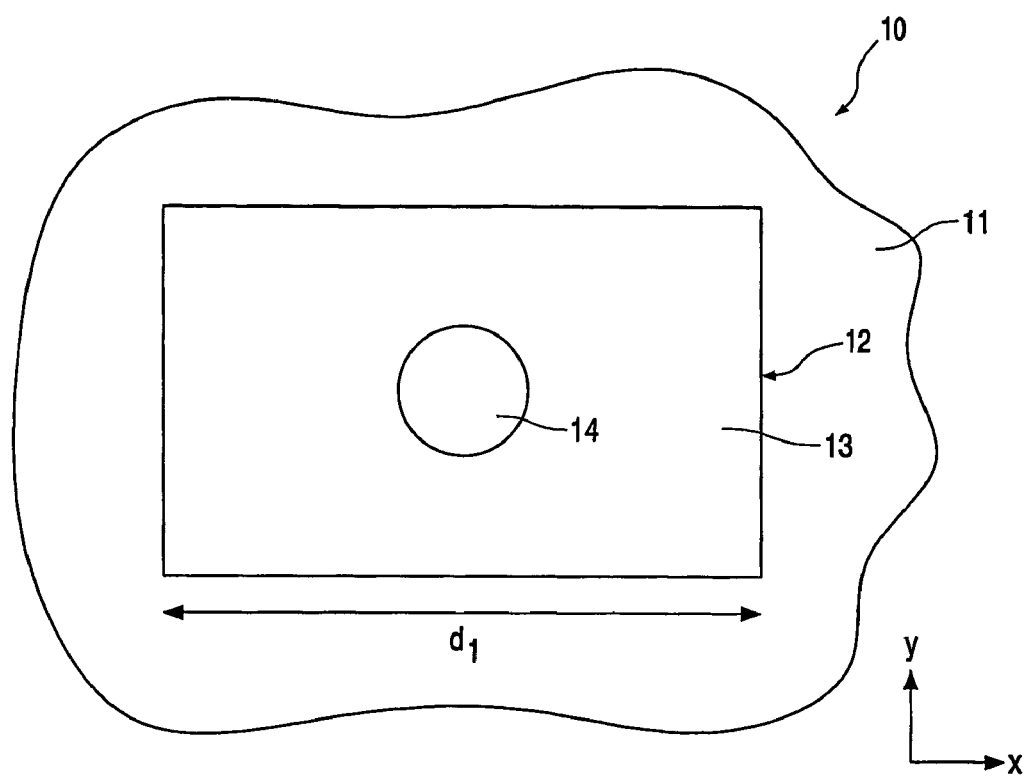
FIG. 1 shows a first embodiment of an electrode arrangement made in accordance with the present invention.

It should be noted that the drawings are diagrammatic and not drawn to scale. Relative dimensions and proportions of parts of the figures have been shown exaggerated or reduced in size for the sake of clarity and convenience in the drawings. The same reference signs are generally used to refer to corresponding or similar features in the different embodiments.

The first illustrated embodiment of a fabric electrode arrangement 10 is shown located on a textile article 11 (part shown), the electrode arrangement including an electrically conductive electrode portion 12 exhibiting a first surface 13 and a portion of material 14 located on the first surface 13. The first surface 13 and the material 14 are intended to contact the skin of a wearer during electrode use. The portion of material 14 is substantially impermeable to moisture and is electrically conductive. In this example the portion of material 14 is of silicon rubber loaded with carbon black. The portion of material 14 is 1.2 mm thick, has a surface area of 0.035 $m^2$ for presenting to the wearers skin during electrode use and exhibits an electrical resistance of 120 Ohms per square.

Ideally, the resistance measured across the thickness of the portion of the material 14 should be as low as possible but may be in the order of 10's of Ohms or lower, but ideally less than 200 Ohms or so. By thickness it is meant that dimension between the surface of portion 14 which contacts the wearers skin and the surface of portion 14 which contacts the first surface 13 of conductive electrode portion 12.

The electrically conductive electrode portion 12 is of knitted construction. More specifically the first embodiment is of plain knit structure using yarn comprising tactel™ (a type of nylon) which is an electrical insulator and stainless steel which is an electrical conductor. The yarn is a staple yarn and comprises 20%-30% of the stainless steel. As illustrated in FIG. 1, the yarn is knitted to extend in the direction denoted x.

The electrical resistance of the conductive electrode portion 12 when measured lengthways over distance denoted $d_1$ in FIG. 1 is in the region of 20 Ohms to 40 Ohms but in any case in the region of 10's of Ohms. Distance $d_1$ is 0.065 m.

The need to reduce the electrical resistance between the users skin and the conductive electrode portion 12 could be met to some extent by increasing the percentage of conductive material in the electrode portion 12. This could be done by increasing the percentage of stainless steel in the yarn used to knit the electrode or by introducing a further yarn having conductive qualities. However, manufacturing constraints can impose a limit on the amount of conductive material that can be included in the knit. Furthermore, as the amount of conductive material is increased the electrode portion 12 takes on a feel that is progressively dissimilar to the textile article 11 that it is integrated with and becomes less flexible and less comfortable when worn against the users skin.

The electrically conductive electrode portion 12 may be sewn, glued or otherwise attached to the textile article 11. Alternatively the electrically conductive electrode portion 12 may be an integral part of the textile article 11. In the latter case, where the textile article 11 is of knitted construction the electrode portion 12 may also be of knitted construction and formed during the same production process merely by appropriate selection of electrically conductive yarn during knitting of the article to define the electrode portion. Intarsia and jacquard techniques may also be used, or the conductive yarn may be "laid in".

The portion of conductive moisture impermeable material 14 is attached to the electrode portion 12 by suitable electrically conductive adhesive but may be attached by other means such as heat bonding (partially melting: the impermeable material onto the electrode portion 12), ultrasonic welding, sewing or other means as will be appreciated by the person skilled in the art. In certain cases the conductive properties of material 14 may permit attachment by inductive welding.

Figure 2:
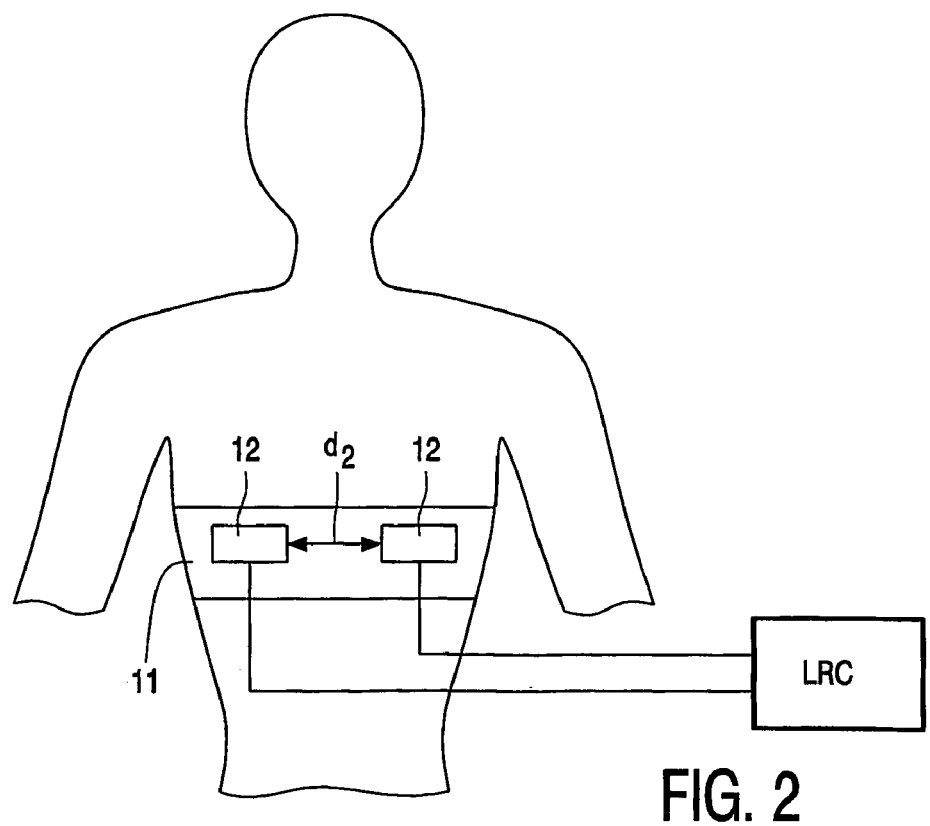
FIG. 2 shows a schematic arrangement of an electrode arrangement of the present invention positioned on a wearer and electrical resistance measuring equipment.

Measurement of the electrode to skin electrical contact impedance was conducted using the setup shown schematically in FIG. 2. A garment in the form of a fabric band 11 is worn around the chest of the torso and is provided with an electrode arrangement having two conductive electrode portions 12 such that when the band is worn correctly, one electrode portion 12 is positioned on one front side of a wearers chest and the other electrode portion 12 is located on the other front side of the wearers chest. Each electrode portion 12 is provided with a portion of material 14 (not shown) that is impermeable to moisture and electrically conductive, as already described with reference to FIG. 1. The electrodes 12 are rectangular in shape each with a height of 0.02 m and a width of 0.065 m as viewed while the garment 11 is appropriately worn, for example as shown in FIG. 2. The shortest spacing between the electrodes is 0.01 m which is denoted in FIG. 2 as $d_2$. Each electrode portion 12 and moisture impermeable portion 14 is held in contact with the wearers skin by the band 11 during measurement.

A first one of the electrode portions 12 was connected to one measurement lead of an inductance, resistance and capacitance (LRC) meter while a second one of the electrode portions 12 was connected to another one measurement lead of the meter. A 120 Hz measurement signal was applied to the electrode portions and the impedance across the two electrodes was measured. For the avoidance of doubt each electrode was physically separated from the another but both were placed in contact with a different portion of the wearers skin.

Figure 3:
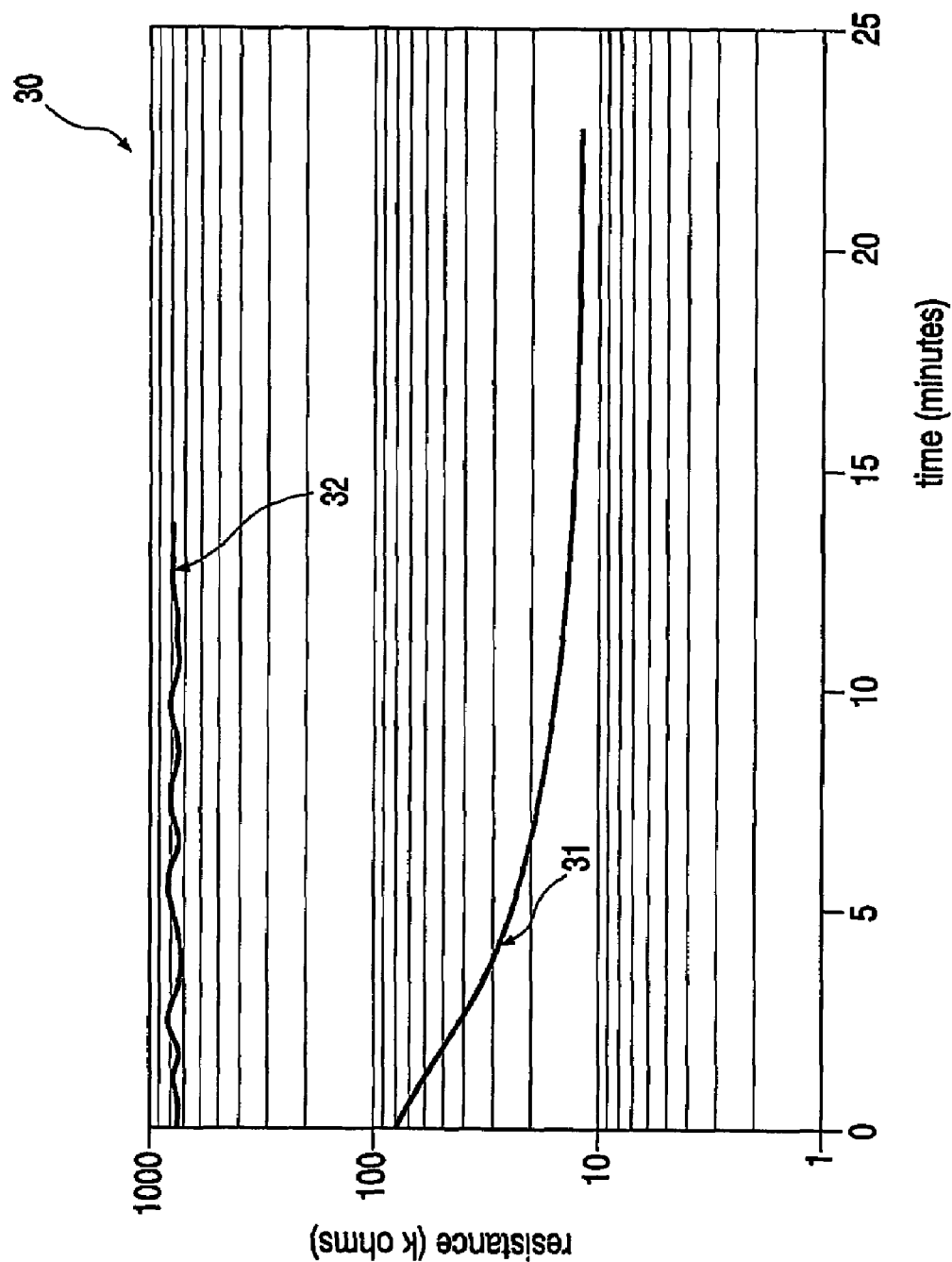
FIG. 3 shows plots of electrical resistance measured across two electrodes of an electrode arrangement placed in contact with a wearers skin.

The resistance component of the measured impedance is shown in FIG. 3; this measurement being total series resistance of a first electrode portion 12 in contact with the users skin and a second electrode portion 12 in contact with another part of the users skin. Assuming the major component of the impedance is present at the electrode-to-skin interfaces, and in comparison impedance within the body is low, an approximate indication of the electrode-to-skin impedance of one electrode can be reached by dividing the measured values by a factor of two.

Graph 30 shown in FIG. 3 has a linear x axis of time in minutes and a logarithmic y axis of resistance in kilo ohms. The measurements were started once the electrodes had been attached to a wearer and the electrical resistance component of the measured impedance is shown by plot line 31. As can be seen initial measured resistance was in the order of 80 k Ohms failing to around 25 k Ohms after 5 minutes of continual wearing, approximately 15 k Ohms after 10 minutes of wearing and levelling off at around 12 k Ohms after 20 minutes of wearing. These measurements were taken with the wearer sitting down and the reduction of resistance over time is due to moisture forming between material portion 14 and the wearers skin to reduce the electrical resistance at the component 14 and skin interface.

To form a comparison the same set-up of FIG. 2 was used with knitted electrodes of the same type and dimensions but not having the component 14 of moisture impermeable conductive rubber. The electrical resistance component of the measured impedance is shown by plot line 32. In this case the measured resistance is much higher, in the order of 750 k Ohms to 850 k Ohms for the first 15 minutes of use for which measurements were available.

The reduced electrical resistance or impedance of the electrode arrangement 10 improves the process of detecting electrical signals from a wearers body. The improvement is realised because during early stages of wearing the electrode arrangement the formation of perspiration between the skin and the moisture impermeable material 14 reduces electrical resistance between the skin and material 14. The electrical resistance between the material 14 and knitted conductive electrode portion 12 is already low due to design of the electrode arrangement and so a path of relatively low electrical resistance is established between the skin and conductive electrode portion 12 via the material 14. The said path certainly has a lower electrical resistance in comparison with the electrical resistance of a comparable direct skin-to-electrically conductive textile portion 12 interface, especially when the wearers skin is dry. In fact, the nature of the knitted conductive electrode portion 12 is such that it tends to absorb and dissipate user perspiration while letting the users skin breathe. While these effects contribute to user comfort when wearing the electrode having a textile conductive electrode portion 12, they also raise the skin to electrode contact resistance, at least until a wearer has performed enough exercise to generate considerable perspiration to moisten the electrode portion 12. Thus, the portions of electrically conductive material 14 that are impermeable to moisture define regions of the electrode arrangement where a relatively low amount of perspiration serves to reduce electrode to skin electrical resistance.

Although electrical resistance between the users skin and fabric portion 12 is quite high, the electrical resistance within electrode conductive portion 12 is relatively low, that is in the region of 20 Ohms to 40 Ohms when measured along length denoted $d_1$. Therefore, the combined effect of a conductive electrode portion 12 having a resistance of 10's of Ohms and an impermeable conductive portion 14 having a resistance across its thickness of a few 10's of Ohms provides an efficient arrangement for detecting electrical signals of a user. By making the moisture impermeable portion 14 thin, efficiency can be improved and/or materials having a higher bulk resistivity can still be used to form portion 14.

Although the arrangement of the first embodiment is described with the portion of electrically conductive moisture impermeable material 14 attached to the conductive electrode portion 12, the attachment does not need to be direct and there may be one or more layer of electrically conductive material between the material 14 and portion 12. Furthermore attachment of the moisture impermeable material 14 to portion 12 is not mandatory because mere appropriate location of material 14, such that during use material 14 electrically contacts portion 12, either directly or indirectly, is sufficient to allow operation in accordance with the present invention.

Figure 4A:
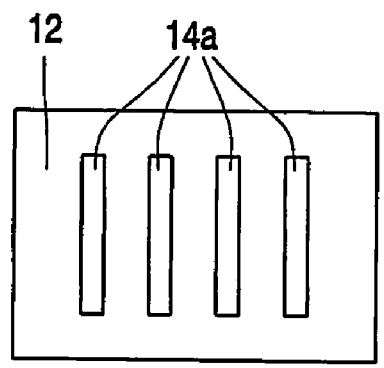
FIGS. 4a-4c show further embodiments of an electrode arrangement made in accordance with the present invention.
Figure 4B:
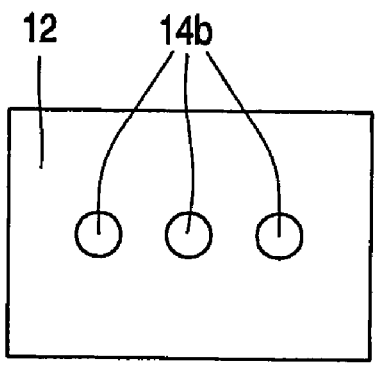
Figure 4C:
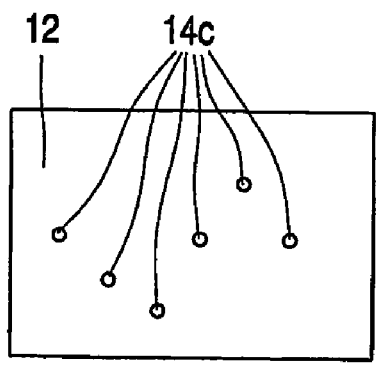

FIGS. 4a-4c show further embodiments of the present invention where the single circular portion of conductive moisture impermeable material 14 has been replaced by other arrangements of such material. In FIG. 4a electrode portion 12 is provided with one or more substantially rectangular portions of conductive moisture impermeable material 14a. In FIG. 4b electrode portion 12 is provided with two or more substantially circular portions of conductive moisture impermeable material 14b. In FIG. 4c electrode portion 12 is provided with a plurality of circular portions 14c of conductive moisture impermeable material, each of the portions 14c being appreciably smaller in terms of the surface area they present to the users skin during use than the area presented by portion 14 of the first embodiment shown in FIG. 1. However the or each portion 14 of electrically conductive moisture impermeable material needs to be of a shape and size adequate to encourage the skin it covers to perspire; too small an area or too narrow the portion and perspiration will not be encouraged and trapped in the manner required to reduce electrode to skin resistance as described above.

While the present invention has been discussed with reference to a knitted electrode structure this is not a limiting feature of the present invention which has use in textile based electrodes in general, whether the electrodes are of a knitted, woven, embroidered, or non-woven structure. Furthermore, although the present invention has been described in the context of detecting signals from the body of a wearer, the electrodes could also be used for application of electrical current to a mammal.

In most cases the present arrangement will obviate the need for a user to actively wet an electrode component for correct operation. However, in some cases, depending on the user, it may be necessary to provide some supplementary moisture, for example by wetting the moisture impermeable conductive portions 14. Even where such supplemental wetting is required, less moisture will be required to do this than would be the case when wetting fabric portion 12 and the moisture impermeable portions are less prone to drying out than fabric conductive portions 12 and so correct operation can be expected for a longer period than an arrangement without the impermeable conductive portions 14.

From reading the present invention other modifications will be apparent to persons skilled in the art. Such modifications may include other features which are already known in the design, manufacture and use of fabric based electrodes, signal processing circuitry, garment construction and materials and applications thereof and which may be used instead of or in addition to features already described herein.

The invention claimed is:

1. An electrode arrangement comprising:
   an electrically conductive fabric having a first surface for application to skin of a mammal; and
   at least one portion of material which is substantially impermeable to moisture, said material being located on said first surface,
   wherein said electrically conductive fabric is integral with a garment.

2. The electrode arrangement in accordance with claim 1 wherein said atleast one portion of material is located directly on said first surface.

3. The electrode arrangement in accordance with claim 1 wherein said material is mechanically flexible.

4. The electrode arrangement in accordance with claim 1 wherein said material is silicone rubber loaded with conductive material.

5. A garment comprising:
   a wearable article of clothing; and
   a fabric electrode arrangement exhibiting a first surface for application to skin of a mammal wearing the article of clothing, the fabric electrode arrangement being disposed on an inner surface of the article of clothing with the first surface facing inward, said fabric electrode arrangement including:
   at least one portion of material which is substantially impermeable to moisture, said moisture impermeable material being located on said first surface; and
   an electrically conductive, moisture permeable fabric portion located on the first surface around the substantially moisture impermeable portion of material.

6. The garment in accordance with claim 5 wherein the moisture impermeable portion is electrically conductive and flexible.

7. The garment in accordance with claim 6 wherein the fabric electrode arrangement is free of electrically conductive gel with only perspiration induced by the moisture impermeable portion acting as a sole skin-to-electrode contact resistance reducing agent.

8. An electrode arrangement comprising:
   an electrically conductive fabric portion with a first surface which contacts a wearer's skin directly;
   a moisture impermeable, electrically conductive layer affixed to the first surface of the electrically conductive fabric to contact the wearer's skin directly, such that said layer promotes perspiration which reduces skin-to-electrode contact resistance and such that the electrically conductive fabric absorbs and dissipates perspiration while permitting the skin to breathe to promote user comfort.

9. The electrode arrangement in accordance with claim 8 wherein the moisture impermeable, electrically conductive layer contacts the skin directly with only perspiration functioning to reduce the skin- to-electrode contact resistance.

10. The electrode arrangement in accordance with claim 8 wherein the moisture impermeable, electrically conductive layer and the electrically conductive fabric are both flexible.

11. The electrode arrangement in accordance with claim 8 wherein the moisture impermeable, electrically conductive layer includes silicone rubber filled with a conductive material.

12. The electrode arrangement in accordance with claim 11 wherein the conductive material includes one of carbon and silver.

13. The electrode arrangement in accordance with claim 8 wherein the electrically conductive fabric is knitted or woven.

14. The electrode arrangement in accordance with claim 13 wherein the electrically conductive fabric is knitted or woven from electrically conductive fibers and non-conductive fibers.

15. A wearable article comprising:
    a garment made of non-electrically conductive fabric; and
    one or more electrode arrangements in accordance with claim 8, positioned on the garment to contact the wearer's skin.

16. A textile article comprising:
    a non-electrically conductive fabric; and
    one or more electrode arrangements in accordance with claim 8, in which the electrically conductive fabric portion is supported by the non-electrically conductive fabric and positioned to contact the wearer's skin.

* * * * *